(12) United States Patent
Forstner (10) Patent No.: US 9,724,046 B2
(45) Date of Patent: Aug. 8, 2017

(54) DETECTING APPARATUS FOR ARRHYTHMIA AND DETECTING METHOD OF THE DETECTING APPARATUS

(71) Applicant: Rossmax International Ltd., Taipei (TW)

(72) Inventor: Klaus Forstner, Asperg (DE)

(73) Assignee: ROSSMAX INTERNATIONAL LTD., Taipei (TW)

( * ) Notice: Subject to any disclaimer, the term of this patent is extended or adjusted under 35 U.S.C. 154(b) by 64 days.

(21) Appl. No.: 14/926,165

(22) Filed: Oct. 29, 2015

(65) Prior Publication Data

US 2016/0128640 A1     May 12, 2016

(30) Foreign Application Priority Data

Nov. 12, 2014   (TW) .............................. 103139201 A (51) Int. Cl.
*A61B 5/0464*     (2006.01)
*A61B 5/00*       (2006.01)
(Continued)

(52) U.S. Cl.
CPC ............ *A61B 5/7275* (2013.01); *A61B 5/022* (2013.01); *A61B 5/024* (2013.01);
(Continued)

(58) Field of Classification Search
CPC . A61B 5/7275; A61B 5/02405; A61B 5/1107; A61B 5/7282; A61B 5/7264;
(Continued)

(56) References Cited

U.S. PATENT DOCUMENTS 6,519,490 B1 *   2/2003   Wiesel ................... A61B 5/046
                                                       600/518
2001/0049476 A1   12/2001  Forstner
(Continued)

FOREIGN PATENT DOCUMENTS

EP          1195133 A2     4/2002
GB          2448975 A     11/2008
JP       2002017687 A      1/2002

OTHER PUBLICATIONS

Search Report dated Jan. 26, 2016 of the Corresponding European Patent Application No. 15192871.0.

*Primary Examiner* — Michael Carey
(74) *Attorney, Agent, or Firm* — Chun-Ming Shih; HDLS IPR Services (57) ABSTRACT

An apparatus (1) and method for detecting pulse-related parameters, such as pulse arrhythmia is presented. The apparatus (1) detects a series of pulses from a user, e.g. through a cuff-related measurement. Time differences, amplitude and pattern differences between multitudes of N pulses are determined. The apparatus investigates the degree of similarity of multiple pulse periods and/or pulse amplitudes and/or pulse pattern and subsequently generates a statistical set of similarity values based on a plurality of compared results. Basing on this, the apparatus generates a decision value based on the statistical sets of similarity values, and uses the decision value to determine whether or not the user discloses a normal pulse rhythm, atrial fibrillation, premature atrial or ventricular contractions, tachycardia, bradycardia and/or unspecified pulse arrhythmia. Further an artefact index is generated, informing the user whether a measurement was taken under sufficient artefact-free measurement conditions.

18 Claims, 4 Drawing Sheets

(51) Int. Cl.
*A61B 5/024* (2006.01)
*A61B 5/022* (2006.01)
*A61B 5/11* (2006.01)
*A61B 5/021* (2006.01)
*A61B 5/0255* (2006.01)
*G06F 19/00* (2011.01)

(52) U.S. Cl.
CPC ...... *A61B 5/02405* (2013.01); *A61B 5/02422* (2013.01); *A61B 5/1107* (2013.01); *A61B 5/7246* (2013.01); *A61B 5/7264* (2013.01); *A61B 5/7282* (2013.01); *A61B 5/742* (2013.01); *A61B 5/0255* (2013.01); *A61B 5/02141* (2013.01); *G06F 19/345* (2013.01)

(58) Field of Classification Search
CPC ... A61B 5/02422; A61B 5/7246; A61B 5/742; A61B 5/024; A61B 5/022; A61B 5/02141; A61B 5/0255; G06F 19/345
USPC ................ 600/508, 515, 516, 517, 518, 519
See application file for complete search history.

(56) References Cited

U.S. PATENT DOCUMENTS

2008/0269626 A1* 10/2008 Gallagher .......... A61B 5/02416
600/509
2013/0060110 A1* 3/2013 Lynn ..................... A61B 7/003
600/324

\* cited by examiner

DETECTING APPARATUS FOR ARRHYTHMIA AND DETECTING METHOD OF THE DETECTING APPARATUS

TECHNICAL FIELD

This innovation relates to detecting apparatus and detecting methods, particularly relates to the detecting apparatus and detecting methods of detecting arrhythmia.

PRIOR ART

The heart generates autonomously cardiac contractions by a physiologic pacemaker (atrial sinus node) and conducts the electric excitation on specific and well defined tissue pathways to the entry sites, which subsequently generates a mechanical contraction on the heart. Atrial contractions are succeeded by the ventricular contractions, which eject blood to the aorta and to the pulmonal arteries. With each ejection volume of blood, which is called the stroke volume, a mechanical pulse travels along the arteries and can be peripherally picked up by pulse-detecting technologies. One of these technologies is the detection of pulses by the compression of a pre-pressured cuff which is wrapped around the limb and thus is responding to any circumferential pressure changes.

Cardiac pulses normally will be occurring periodically and will have similar pattern (including amplitudes) if the cardio-circulatory system is in a sufficient steady state condition. This is a precondition for indirect blood pressure measurement technologies, thus as the auscultation and the oscillometry.

A large number of cardiac and extra-cardiac impairments may alter the periodicity and the similarity of pulse pattern in patients. Underlying reasons include disorders of the cardiac function, the autonomous cardio-circulatory control, mental or physical stress and pharmacological interferences. In these cases disorders of the pulse rhythm and pulse amplitude similarity and, —in specific cases, of the pulse pattern—, can be monitored.

If these disorders are measured by the electrical signal of the heart, the disorders are called cardiac arrhythmia. If they are detected at the site of the peripheral pulse, these disorders are called pulse arrhythmia.

Clinical arrhythmia occur in specific types, such fast heartrate (Tachycardia, TC), low heartrate (Bradycardia, BC), Atrial Fibrillation (AF), Premature Contractions (PC) and other forms.

Atrial fibrillation is a medical condition, in which the atria aren't synchronously contracting but are limited to a shivering movement. Thus there is no synchronous filling of the ventricles but an infrequent instream of blood to the ventricles, subsequently leading to a high variation in both the pulse period and the stroke volume. Characteristically, the pulse patterns are similar, while pulse amplitudes and pulse periods vary highly in the observation intervals.

Atrial fibrillation may occur as an attack (paroxysmal manifestation), may persist or may stay permanently. Sudden onsets of atrial fibrillation attacks significantly affect the patient's well-being and need immediate treatment. Chronic (Permanent) atrial fibrillation may be tolerated with a limitation of the cardiac function. Atrial fibrillation is age-related, and amongst others may be caused by a coronary heart disease, a valvular heart disease, by a myocardial heart disease, by medication side-effects, by long-term arterial hypertension and by caffeine and nicotine intake. Chronic atrial fibrillation is associated with an elevated probability of suffering from an arterial embolus, which can result in a brain stroke, a peripheral atrial vessel occlusion and/or a myocardial infarction.

The physiological generation of the cardiac excitation is the sinusnode, which is located in the left atrium. However, and pathological conditions, an early impulse can be generated, which leads to an untimely extra-beat. This is called a premature contraction or an extra-systolic contraction. Once the faulty excitation happens to be in the atrium an atrial ventricular contraction occurs, once the excitation derives from a ventricular site, a ventricular contraction is generated. Premature contractions are pathologic. Once they rarely occur and have no repetition pattern, most patients do not notice these extra-beats.

Once an extra-beat is generated early-on, the normal filling of the ventricle is not completed. Thus there is a small stroke volume, which leads to a small pulse volume. Once the ectopic generation happens near the aortal valve or comes in significantly early, the stroke volume is very small and a peripheral pulse cannot be detected anymore. This is noticed as a missing pulse during pulse palpitation or by other pulse detecting technologies.

Ventricular contractions may go unnoticed, but also can be associated to symptoms of variable degree: Dizziness, shortness-of breath, weakness can be followed by spells of fainting (syncope). The most important medical danger is the fact that ventricular contractions may trigger ventricular fibrillation, which poses an immediate life-threatening situation, which needs immediate treatment. Thus the knowledge about ventricular contractions is important for patients with specific risk profiles.

Both disorders, atrial fibrillation as well as ventricular/atrial contractions may go unnoticed and thus establish a latent danger to the health of the patients. The standard diagnosis of cardiac arrhythmia is provided with the derivation of the electrocardiogram. This method however is only performed once suspicious observations have been diagnosed.

The presented PARR technology is a method which is able to detect amongst others specific pulse arrhythmia, such as tachycardia, bradycardia, ventricular/atrial contractions and atrial fibrillation in the course of pulse-based, such as oscillometric blood pressure measurement.

The patient obtains an information whether or not one of the given pulse arrhythmia types is present at the point of time of the blood pressure measurement.

The diagnosis with the innovation presented leads to a comprehensive patient instruction, such as:
1> Accept;
2> Make an appointment to see a doctor;
3> See a doctor immediately/Emergency.

SUMMARY OF THE INVENTION

The present invention provides an apparatus and method for detecting arrhythmia of the pulse waveform seen in patients, i.e. an apparatus and method for detecting irregular heartbeat. The purpose of this invention is to detect the possible presence of atrial fibrillation, premature contraction, tachycardia or bradycardia. The present invention also provides a method to detect specific patterns of pulses, e.g. atrial fibrillation and premature contraction when taking blood pressure measurement. Basic blood pressure measurement technology may be oscillometric or non-oscillometric methodology, this method of measuring patients' blood pressure in a particular time.

In order to achieve the above object, the present invention is to get a pulse sequence from cuff of detection apparatus, and from the recorded pulse sequence determine N pulse period and amplitude difference. Detection apparatus runs statistical analysis for determining the similarity and determines a judgment value, on the basis of this value to confirm whether test subjects have atrial fibrillation, premature contraction, tachycardia or bradycardia.

Compared to methods of calculating the average of all pulse periods in the related art, the present invention is to compare sequentially the similarity of two pulse periods and/or pulse amplitudes, can more accurately determine whether the subjects have arrhythmias. Meanwhile, since the invention is not to add up all pulse periods and/or pulse amplitudes and then calculate the average, it can be distinguished from subjects' arrhythmia is atrial fibrillation, premature contraction or other type of arrhythmia. Therefore, compare with the relevant detection technology, the present invention provides the more clear information of detection, thus improving the use of the subjects' wishes.

Also, the present invention is to detect the severity of arrhythmia is to determine the value of the following parameters combination:

(1) Arrhythmia types;
(2) Statistical significance of detection;
(3) The number of pulses during a measurement;
(4) Detection of pulse arrhythmia types.

EMBODIMENT

A preferred example of this present invention, with the diagrams, is described in detail afterward.

Figure 1A:
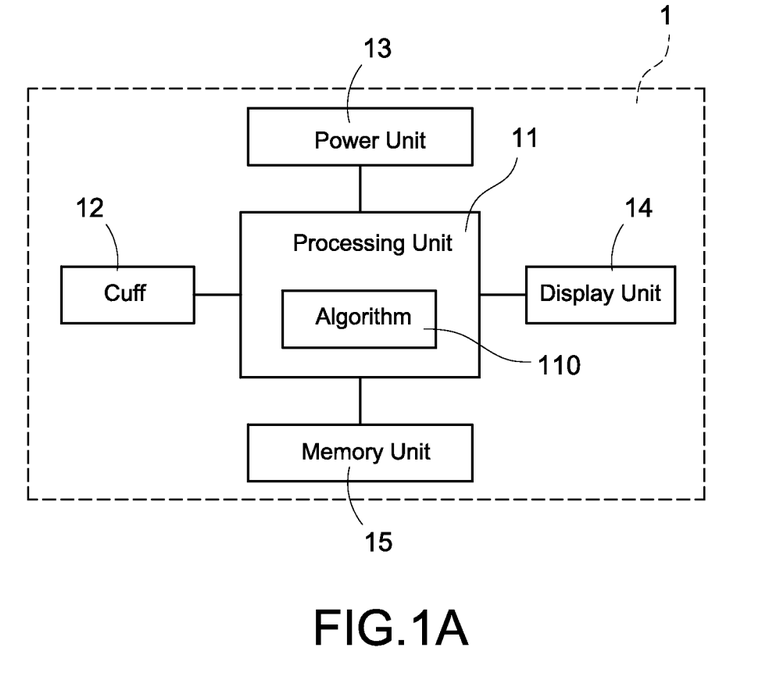
FIG. 1A is a block diagram of detection apparatus of a first embodiment of the present invention.

Referring to FIG. 1A, is a block diagram of detection apparatus of the first embodiment of the present invention. The present invention discloses a cardiac arrhythmia detection apparatus 1, the detection apparatus 1 detects a subject's pulse sequence (series on N pulses), and according to multitude pulse signals to determine multitude pulse time difference and amplitude difference, then gets the plurality of pulse periods and pulse amplitudes, and analyzes whether subjects have arrhythmia. Meanwhile, the detection apparatus 1 also analyzes subjects' heart rate on the basis of detected pulse signals for processing additional analysis. In a preferred embodiment, the detection apparatus 1 may be an electronic sphygmomanometer.

As shown in FIG. 1A, the detection apparatus 1 includes a processing unit 11, a cuff 12, a power unit 13, a display unit 14 and a memory unit 15. The processing unit 11 is electrically connected with the cuff 12, the power unit 13, the display unit 14 and memory unit 15. The processing unit 11 has an algorithm 110, the processing unit 11 can read and execute the algorithm 110, an arrhythmia detection method of the present invention is further executed (detailed contents describe afterwards).

The cuff 12 is mainly an inflatable cuff, which is wrapped in arm of the subjects (usually upper arm, but not be limited). When carrying out pulses detection, the processing unit 11 controls the cuff 12 inflates to a first target pressure. Subsequently, when the processing unit 11 controls the cuff 12 deflates and fixed at a second target pressure, the cuff 12 can detect plurality stably of multitude pulse periods and pulse amplitudes (pulse periods and pulse amplitude sequence). The action of detecting pulses to be target duration (e.g. 30 seconds, 1 minute, 2 minutes . . . etc.) and detect pulse sequence successfully, the processing unit 11 controls the cuff 12 fully deflated, and the pulses detection is completed.

The processing unit 11 receives the measured pulse sequence by the cuff 12, and collects the plurality of pulse sequence of pulse periods and pulse amplitudes. In the present invention, the processing unit 11 mainly executes the algorithm 110 by the plurality of pulse periods and/or pulse amplitudes in order to analyze whether the subjects have arrhythmia (detailed contents describe afterwards). In the present invention, the processing unit 11 is only able to analyze the pulse periods, or analyze the pulse amplitudes, or analyze both of pulse periods and pulse amplitudes, is not to be limited.

Also, the processing unit 11 can calculate the heart rate (beats per minute, bps) of subjects on the basis of measurement time and the number of pulse signals of the pulse sequence. Meanwhile, according to the calculated heart rate, as well as analysis of the duration of each pulse period, the processing unit 11 can analyze whether the subjects have tachycardia (TC) or bradycardia (BC).

The power unit 13 supplies necessary electric power for the detection apparatus 1 and mainly is batteries. In other embodiments, the power unit 13 also can be a power cord, plug to mains in order to obtain necessary electric power for running the detection apparatus 1. Furthermore, the detection apparatus 1 can be connected to other electronic apparatus by the power unit 13, and obtain necessary electric power for running detection apparatus 1 from other electronic apparatus.

The display unit 14 may be a light emitting diode (LED) or liquid crystal display (LCD). The display unit 14 is used for demonstrating the detection results of the detection apparatus 1. If the display unit is LED, it can display different results by different colors (e.g. normal pulse in blue, premature contractions in yellow, atrial fibrillation in red), furthermore, the display unit 14 also can be a display matrix of LEDs, and the display matrix demonstrates the detection results, e.g. heart rate, systolic blood pressure, diastolic blood pressure and so on.

Also, if the display unit 14 is LCD, it can directly in digital, text or graphical display the detection results and detection values of the detection apparatus 1.

The memory unit 15 is used to record the results and/or values of the detection apparatus 1. If the detection apparatus 1 is equipped with a printing unit, the results and/or values can be printed for subjects to retain. Plus, if the detection apparatus 1 is equipped with an Internet connection unit, the results and/or values can be uploaded to a cloud server to save, or sent to subjects' mobile devices directly.

Figure 1B:
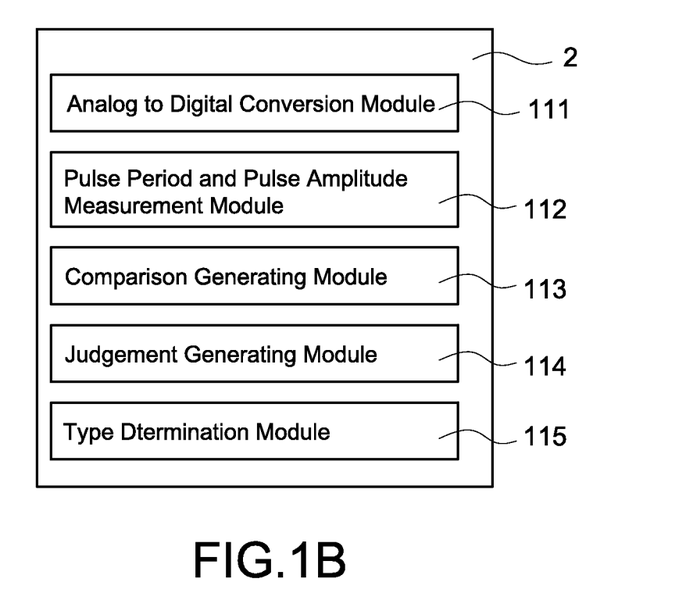
FIG. 1B is a schematic view of processing unit of the first embodiment of the present invention.

Referring to FIG. 1B, is a schematic view of processing unit of the first embodiment of the present invention. As shown in FIG. 1B, according to the executions for each respective portions of the algorithm 110, the processing unit 11 can be divided into an analog to digital conversion module 111, a pulse period and pulse amplitude measurement module 112, a comparison generating module 113, a judgment generating module 114 and a type determination module 115. The function of these modules 111 to 115 are described next.

The detection apparatus 1 detects the pulse sequence the pulse period and the pulse amplitude) of the subjects by the cuff 12, thereby determining the multitude time and amplitude difference. The processing unit 11 obtains the pulse sequence by the cuff 12 and execute an analog to digital conversion by the analog to digital conversion module 111 in order to converse analog pulse sequence to digital pulse sequence, whereby the processing unit 11 can do further analysis and processing of the digitized pulse sequence.

Subsequently, the processing unit 11 obtains the plurality of pulse periods and/or pulse amplitudes from the pulse sequence by the pulse period and pulse amplitude measurement module 112. Specifically, each pulse period is present between two pulse signals, and each pulse signal generates pulse amplitude, so the number of the plurality of pulse signals minus one is the number of pulse periods, and the number of the plurality of pulse signals is equal to the number of pulse amplitude. That is, if the pulse sequence includes pulse signals n, it means pulse periods n−1 (i.e. the pulse sequence comprises n−1 pulse periods) and pulse amplitudes n (i.e. the pulse sequence comprises n pulse amplitudes).

The processing unit 11 compares the similarity of two pulse periods and/or two pulse amplitudes sequentially by the comparison generating module 113 and depending on the results of similarity to generate the corresponding similarity statistical comparison value. In this embodiment, the value is either 1 or 0, when the value is 1 means the two compared pulse periods/pulse amplitudes are similar (i.e. the time difference/amplitude difference is small or equivalent), when the value is 0 means the two compared pulse periods/pulse amplitudes are not similar(i.e. the time difference/amplitude difference is large). In other words, when the two compared pulse periods and/or pulse amplitudes are similar, the comparison generating module 113 generates a similarity statistical comparison value of 1 or True; when the two compared pulse periods and/or pulse amplitudes are not similar, the comparison generating module 113 generates a similarity statistical comparison value of 0 or False. When the comparison generating module 113 processes n comparisons, then similarity statistical comparison values are generated.

In this embodiment, the two compared pulse periods and/or pulse amplitudes may be adjacent or not, is not to be limited.

Specifically, the above comparison generating module 113 runs at least one comparison equation, when the comparison generating module 113 input these two compared pulse periods and/or pulse amplitudes into the comparison equation and the comparison equation is established, the comparison generating module 113 identifies the two compared pulse periods/pulse amplitudes are similar and generates the similarity statistical comparison value which is 1; on the contrary, when the comparison generating module 113 input these two compared pulse periods and/or pulse amplitudes into the comparison equation and the comparison equation is not established, the comparison generating module 113 identifies the two compared pulse periods/pulse amplitudes are not similar and generates the similarity statistical comparison value which is 0.

In this embodiment, his comparison equation includes a pulse period comparison equation and a pulse amplitude comparison equation, the comparison generating module 113 inputs these two compared pulse periods into the pulse period comparison equation and checks whether the pulse period comparison equation is satisfied, and generates a similarity statistical comparison value $S_p$ related to the similarity of pulse period based on the comparison result, and inputs these two compared pulse amplitudes into the pulse amplitude comparison equation and checks whether the pulse amplitude comparison equation is satisfied, and generates a similarity statistical comparison value $S_A$ related to the similarity of pulse amplitude based on the comparison result.

The processing unit 11 in the present invention mainly uses all similarity values which are obtained by the similarity statistical comparison values and determination of whether or not multitude consecutive non-similar pulse periods and/or consecutive non-similar pulse amplitudes exist to be the basis for analysis whether the subjects have atrial fibrillation or premature contraction.

The processing unit 11 judges whether all pulse periods and/or pulse amplitudes comparison is completed, and if so, will get a set of similarity statistical comparison values (contains multitude similarity statistical comparison values $S_P$ and/or similarity statistical comparison values $S_A$); if not, then keep on comparing two pulse periods and/or pulse amplitudes until all pulse periods and/or pulse amplitudes comparisons are completed.

Figure 3:
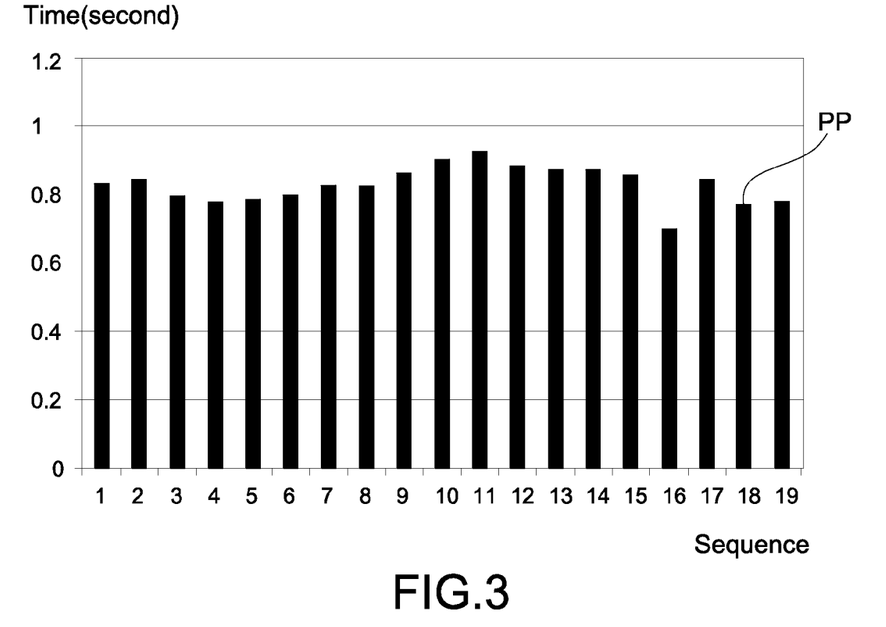
FIG. 3 is a normal pulse period diagram of the first embodiment of the present invention.

Please also refer to FIG. 3 a normal pulse period diagram of the first embodiment of the present invention. FIG. 3 is a chart based on the resulting data of actual detection of a normal heart subject. As shown in FIG. 3, due to the subject's heart rate and pulse are normal, so among the measured pulse sequence, all pulse periods and/or pulse amplitudes are similar to each other(i.e. the comparison equation is satisfied forever), so all the similarity statistical comparison values are 1. However, the present invention described above is only one specific embodiment, should not be limited thereto.

After all the pulse periods and/or pulse amplitudes are compared, the processing unit 11 runs further an analysis and calculation procedure of these similarity statistical comparison values by the judgment generating module 114 and generates one or more judgment values (detailed contents describe afterwards).

The processing unit 11 compares one or more judgment values with one or more threshold values by the type determination module 115. In this embodiment, the one or more threshold values are less than 1 and more than 0 natural numbers. In the present invention, the one or more judgment values may be a pulse period judgment value and/or a pulse amplitude judgment value; the pulse period judgment value can be a coefficient of variation Var ($Z_p$) and/or pulse period average Mean ($PP_i$), the pulse amplitude judgment value can be a coefficient of variation Var ($Z_A$) (detailed contents describe afterwards).

If the pulse period judgment value (Var($Z_p$) or Mean($PP_i$)) is greater than a first atrial fibrillation threshold value AF−1 or a second atrial fibrillation threshold value $PP_{min,AF}$ and/or the pulse amplitude judgment value (Var($Z_A$)) is in between minimum and maximum atrial fibrillation threshold values (AF−$2_{min}$, AF−$2_{max}$), the type determination module 115 may determine whether the subjects are likely to have atrial fibrillation.

Figure 4:
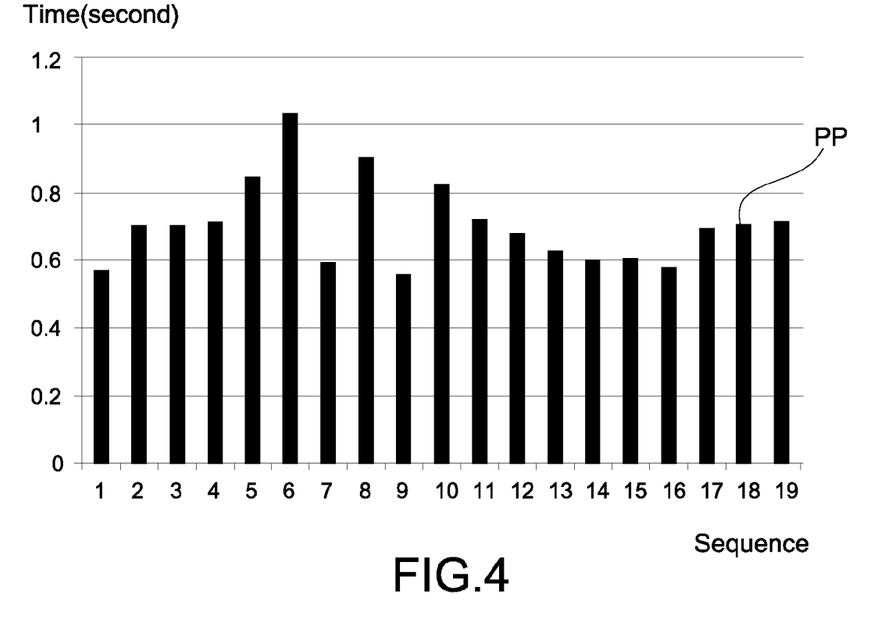
FIG. 4 is an atrial fibrillation pulse period diagram of the first embodiment of the present invention.

Please also refer to FIG. 4, an atrial fibrillation pulse period diagram of the first embodiment of the present invention. FIG. 4 is a chart based on the resulting data of actual detection of an atrial fibrillation subject.

The analysis and calculation procedure referred to above, the judgment generating module 114 adds up the similarity statistical comparison values. Specifically, after n−1 pulse period similarities are established, $Z_P$ different similarities are outputted, and n pulse amplitude similarities are also established, and $Z_A$ different amplitude similarities are also outputted. Where $$Z_P = \frac{1}{2} * \binom{n-1}{2}; Z_A = \frac{1}{2} * \binom{n}{2},$$

whereby the judgment generating module 114 may further calculate the judgment value (the pulse period judgment value and/or pulse amplitude judgment value) described above. If the calculated judgment value is 1, it indicates that the complex similarity statistical comparison values are all 1 (i.e. as shown in FIG. 4 of normal pulse period and/or pulse amplitude); on the other hand, if the judgment value is less than 1, it means that at least one value of the similarity statistical comparison values is 0.

In the present embodiment, when the pulse period judgment value ($Var(Z_P)$ or $Mean(PP_i)$) is greater than the first atrial fibrillation threshold value AF−1 or the second atrial fibrillation threshold value $PP_{min,AF}$ and/or the pulse amplitude judgment value ($Var(Z_A)$) is in between the minimum and maximum atrial fibrillation threshold values ($AF-2_{min}$, $AF-2_{max}$), the type determination module 115 may determine whether the subjects are likely to have atrial fibrillation.

Next, if the pulse period judgment value $Var(Z_P)$ is in between first minimum and maximum premature contraction pulse period threshold values ($APC-1_{min}$, $APC-1_{max}$) and/or the $Var(Z_P)$ is in between second minimum and maximum premature contraction pulse amplitude threshold values ($APC-2_{min}$, $APC-2_{max}$), the type determination module 115 further based on the complex similarity statistical comparison values to determine whether there is multitude consecutive dissimilar pulse periods and/or pulse amplitudes (e.g. $L_{min}$ or above, where $L_{min}$ is equal to or greater than 2). If it does have $L_{min}$ or above consecutive dissimilar pulse periods and/or pulse amplitudes, the type determination module 115 may determine whether the subjects are likely to have premature contraction.

Also, the detection apparatus 1 can keep on determining whether the subjects have other irregular heartbeat. For example, if the pulse period judgment value (such as the $Mean(PP_i)$) is less than a minimum pulse period threshold value ($PP_{min,TC}$), the type determination module 115 may determine that the subjects may have tachycardia. If the pulse period judgment value (such as the $Mean(PP_i)$) is greater than a maximum pulse period threshold value ($PP_{max,BC}$), the type determination module 115 may determine that the subjects may have bradycardia.

Figure 5:
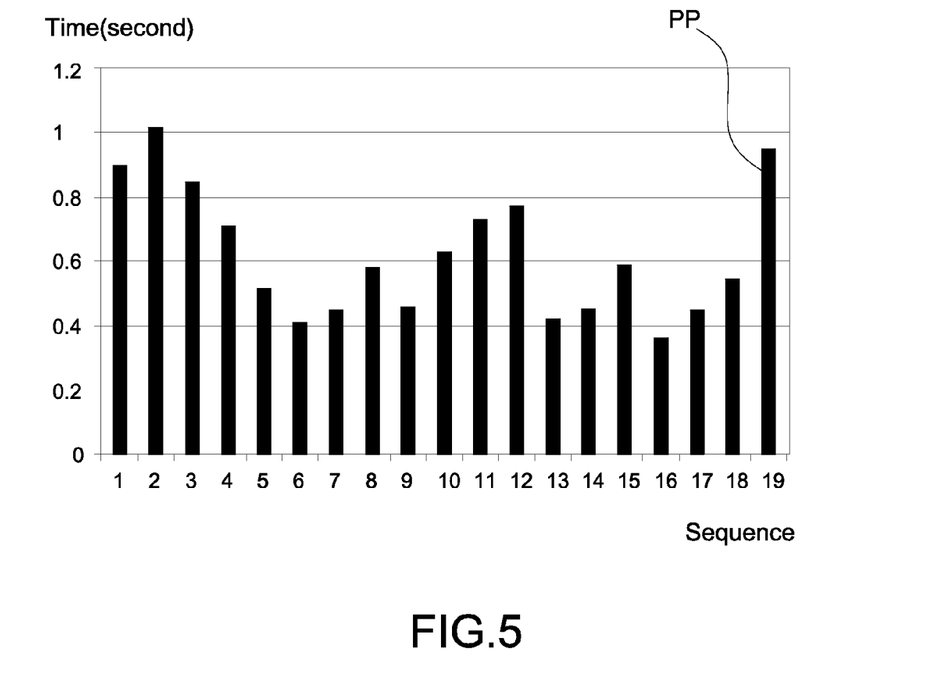
FIG. 5 is a premature contraction pulse period diagram of the first embodiment of the present invention.

Please also refer to FIG. 5, a premature contraction pulse period diagram of the first embodiment of the present invention. FIG. 5 is a chart based on the resulting data of actual detection of a premature contraction subject.

As can be seen from FIG. 5, the subjects who have premature contraction, having the detection result with $L_{min}$ or above consecutive dissimilar pulse periods and/or pulse amplitudes.

In the present invention, the processing unit 11 mainly converts the complex pulse periods and/or pulse amplitudes to these similarity statistical comparison values by the comparison equation, and then calculates these statistic values $Z_p$ and $Z_A$ of the similarity statistical comparison values, and the one or more judgment value which is related to the pulse condition of subjects by the analysis and calculation procedure. In this embodiment, the pulse period comparison equation is as below:

$$S_P(i,j)=(1-K)*PP_i<PP_j<(1+K)*PP_i$$

Where, K is i−j, and K is usually between 0.02 to 0.2; $\lceil S_P \rfloor$ means the similarity statistical comparison value corresponding to similarity of pulse periods. $\lceil PP \rfloor$ means the pulse period between two pulse signals; $PP_i$ is one of the compared pulse periods and i is a positive integer from 1 to n; $PP_j$ is other one of the compared pulse periods and j is a positive integer from 1 to n.

The pulse amplitude comparison equation is as below:

$$S_A(i,j)=(1-L)*A_i<A_j<(1+L)*A_i$$

Where, L is i−j, and K is usually 0.005 to 0.25; $\lceil S_A \rfloor$ means the similarity statistical comparison value corresponding to similarity of pulse amplitudes. $\lceil A \rfloor$ means the pulse amplitude of pulse signal; $A_i$ is one of the compared pulse amplitudes and i is a positive integer from 1 to n; $A_j$ is other one of the compared pulse amplitudes and j is a positive integer from 1 to n.

Figure 2:
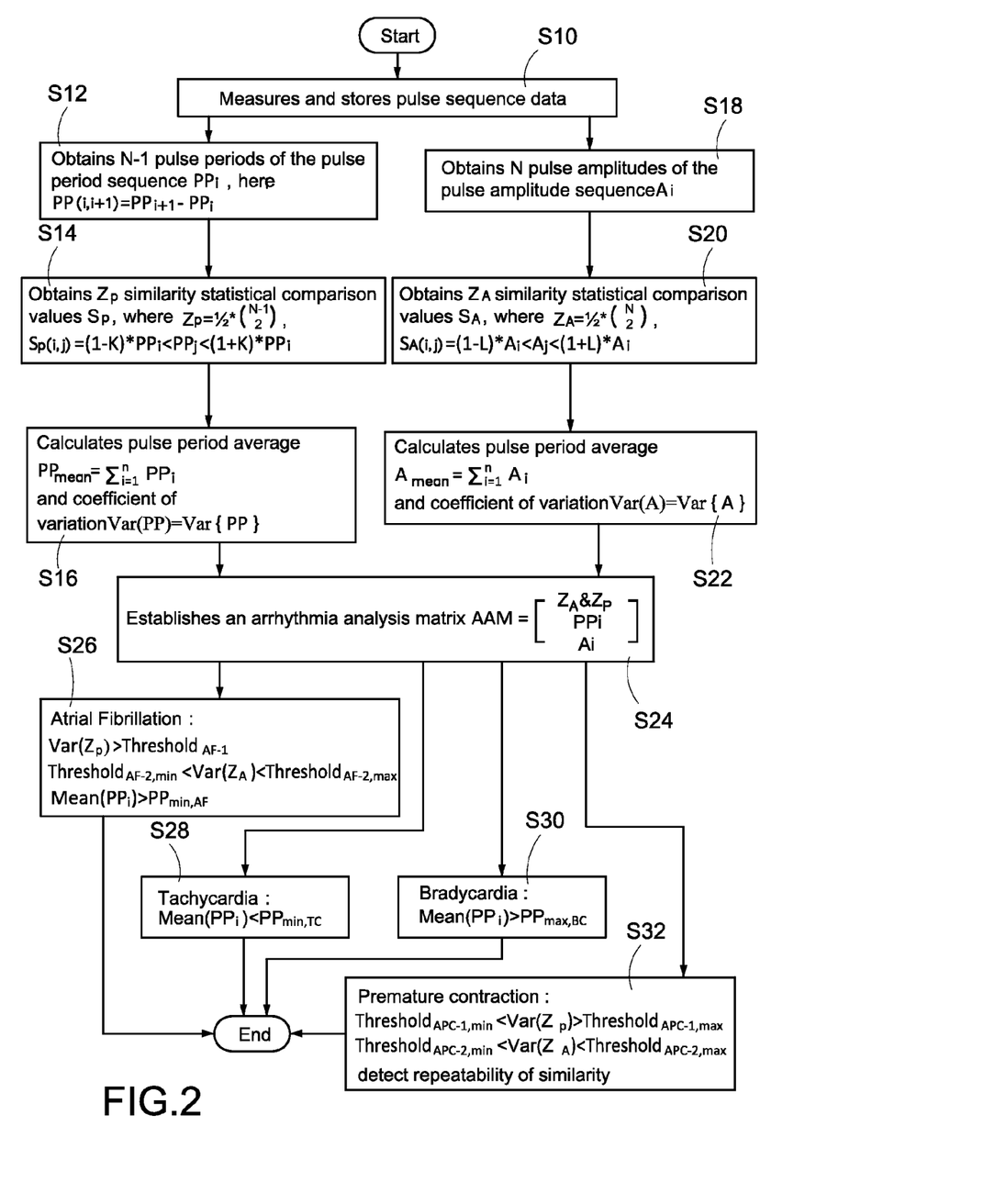
FIG. 2 is a procedure of detecting of the first embodiment of the present invention.

See FIG. 2, a procedure of detecting of the first embodiment of the present invention. The detection procedure shown in FIG. 2 in accordance with the detection apparatus 1 and above comparison equation and analysis and calculation procedure to realize, specifically describe as below.

First, the detection apparatus 1 measures and stores the pulse sequence data of the subjects (step S10), thereby, which can obtain N−1 pulse periods of the pulse period sequence ($PP_i$), where $PP_{(i,i+1)}=PP_{i+1}-PP_i$ (step S12), and can obtain N pulse amplitudes of the pulse amplitude sequence ($A_i$) (step S18). In this embodiment, the detection method can only obtain N−1 pulse periods, or only N pulse amplitudes, or simultaneously obtain N−1 pulse periods and N pulse amplitudes, not be limited.

It is worth mentioning that, in the disclosed detection method of present embodiment, the detection apparatus 1 can obtain the pulse signals by a variety of ways, such as mechanical pressure, optical pulse wave or acoustic pulse detection to detect, or detect other signals of the subjects and then covert to pulse signals, the detection method is not limited to cuff.

Subsequently, while the detection apparatus 1 detects second pulse period $PP_2$, it sequentially determines whether the pulse period comparison equation $(1-K)*PP_i<PP_j<(1+K)*PP_i$ is satisfied; if the pulse period comparison equation is satisfied to generate the similarity statistical comparison value $S_p$, and make this value is 1; if the pulse period comparison equation is not satisfied to generate the similarity statistical comparison value $S_P$, and make this value is 0; the detection apparatus 1 will generate $Z_P$ similarity statistical comparison values $S_P$ of n−1 pulse periods, where $$Z_P = \frac{1}{2} * \binom{n-1}{2} \text{ (step S14).}$$

That is, the $Z_P$ is a statistic value of the similarity statistical comparison corresponding to values $S_p$ similarity of the pulse periods.

Similarly, the detection apparatus 1 detects second pulse amplitude $A_2$, and sequentially determines whether the pulse amplitude comparison equation $(1-L)*A_i < A_j < (1+L)*A_i$ is satisfied; if the pulse amplitude comparison equation is satisfied to generate the similarity statistical comparison value $S_A$, and make this value is 1; if the pulse amplitude comparison equation is not satisfied to generate the similarity statistical comparison value $S_A$, and make this value is 0; the detection apparatus 1 will generate $Z_A$ similarity statistical comparison values $S_P$ of n pulse amplitudes, where $$Z_A = \frac{1}{2} * \binom{n}{2} \text{ (step } S20\text{)}.$$

That is, the $Z_A$ is a statistic value of the similarity statistical comparison values $S_a$ corresponding to similarity of the pulse amplitudes.

Then, the detection apparatus 1 determines whether all of the pulse periods and/or pulse amplitudes comparison is completed. If not, keep on proceeding comparison. When the plurality of pulse periods and/or pulse amplitudes have compared, the detection apparatus 1 will calculate the one or more judgement values, wherein the one or more judgement values can be used as the pulse period judgement values and comprise pulse period average $PP_{mean} = \Sigma_{i=1}^{n} PPi$ and coefficient of variation $Var(PP) = Var\{PP\}$(step S16). And, the one or more judgement values can be used as the pulse amplitude judgement values and comprise pulse amplitude average $A_{mean} = \Sigma_{i=1}^{n} Ai$ and coefficient of variation $Var(A) = Var\{A\}$ (step S22).

A $Z_{total}$ is composed of similarity of these statistic values $Z_A$ and $Z_P$, the judgment generating module 114 of the detection apparatus 1 can also be the basis of $Z_{total}$ value, $A_i$ value of n pulse amplitudes and $PP_i$ value of n pulse periods to establish an Arrhythmia Analysis Matrix (AAM), where $$AAM = \begin{bmatrix} ZP \\ ZA \\ PPi \\ Ai \end{bmatrix} \text{ (step } S24\text{)}.$$

The type determination module 115 of the detection apparatus 1 is accordance with the AAM and a unique threshold statistical analysis, in order to detect (1) atrial fibrillation, (2) premature contraction, (3) bradycardia, (4) tachycardia. Specific analysis is as follows:

(1) Atrial fibrillation:

Statistics $PP_i$, $Z_A$ and $_p$ variation must meet the clinical threshold, wherein when the pulse period judgement value $Var(Z_p)$>the first atrial fibrillation threshold value AF-1, the minimum atrial fibrillation threshold value $AF-2_{min}$<the pulse amplitude judgement value $Var(Z_A)$<the maximum atrial fibrillation threshold value $AF-2_{max}$; and/or the pulse period judgement value $Mean(PP_i)$>the second atrial fibrillation threshold value $PP_{min,AF}$, is determined atrial fibrillation (step S26);

(2) Premature contraction:

The first minimum premature contraction pulse period threshold value $APC-1_{min}$<the pulse period judgement value $Var(Z_p)$>The first maximum premature contraction pulse period threshold value $APC-1_{max}$; the second minimum premature contraction pulse amplitude threshold value $APC-2_{min}$<the pulse amplitude judgement value Var $(Z_A)$>The second maximum premature contraction pulse amplitude threshold value $APC-2_{max}$; and/or detection of repetitive similarity is determined premature contraction (step S32);

(3) Tachycardia:

The pulse period judgement values $Mean(PP_i)$<the minimum pulse period threshold value $PP_{min, TC}$, is determined tachycardia (step S28);

(4) Bradycardia:

The pulse period judgement values $Mean(PP_i)$>the maximum pulse period threshold value $PP_{max, BC}$, is determined bradycardia (step S30).

Furthermore, by above statistical analysis but cannot determine the specific type of arrhythmia, the detection apparatus 1 will classify it as non-specified arrhythmia. The invention effectively distinguishes atrial fibrillation and premature contraction by the detection apparatus 1, the algorithm 110, the comparison equation and the analysis and calculation procedure, thus the results are more accurate.

The above-described preferred embodiment of the invention is not limited to the claimed scope of this invention, so that whenever the content of the present invention is the use of an equivalent changes are included within the scope of the present invention.

What is claimed is:

1. An arrhythmia detecting method adopted in an arrhythmia detection apparatus, comprising:
   a) obtaining a pulse period sequence and a pulse amplitude sequence through a cuff of the arrhythmia detection apparatus, and in which to obtain a plurality of pulse periods and a plurality of pulse amplitudes through a pulse period and a pulse amplitude measurement module of the arrhythmia detection apparatus;
   b) comparing similarities of any two of the pulse periods and any two of the pulse amplitudes for respectively generating similarity statistical comparison values through a comparison generating module of the arrhythmia detection apparatus, wherein each of the generated similarity statistical comparison values is 1 if the two compared pulse periods or the two compared pulse amplitudes are similar, and is 0 if the two compared pulse periods or the two compared pulse amplitudes are dissimilar;
   c) calculating a statistic value comprising a set of the similarity statistical comparison values corresponding to the similarities of the pulse periods and another statistic value comprising a set of the similarity statistical comparison values corresponding to the similarities of the pulse amplitudes through a judgment generating module of the arrhythmia detection apparatus;
   d) establishing an arrhythmia analysis matrix according to the statistic values, the pulse period sequence and the pulse amplitude sequence through the judgment generating module, wherein the arrhythmia analysis matrix (AAM) is $$\begin{bmatrix} ZP \\ ZA \\ PPi \\ Ai \end{bmatrix},$$

where $Z_P$ is the statistic value comprising the set of the similarity statistical comparison values corresponding to the similarities of the pulse periods, $Z_A$ is the statistic value comprising the set of the similarity statistical comparison values corresponding to the similarities of the pulse amplitudes, $PP_i$, is the pulse period sequence, and $A_i$, is the pulse amplitude sequence;

e) determining an atrial fibrillation, through a type determination module of the arrhythmia detection apparatus, when a coefficient of variation $Var(Z_P)$ is greater than a first atrial fibrillation threshold value AF-1, a pulse period average Mean $(PP_i,)$ is greater than a second atrial fibrillation threshold value $PP_{min,\ AF}$ or a coefficient of variation $Var(Z_A)$ is between minimum and maximum atrial fibrillation threshold values (AF-$2_{min}$, AF-$2_{max}$);

f) determining, through the type determination module, if the coefficient of variation $Var(Z_P)$ is between first minimum and maximum premature contraction pulse period threshold values (APC-$1_{min}$, APC-$1_{max}$), or the coefficient of variation $Var(Z_A)$ is between second minimum and maximum premature contraction pulse amplitude threshold values (APC-$2_{min}$, APC-$2_{max}$);

g) determining, through the type determination module, a premature contraction when multitude continuous dissimilar pulse periods or pulse amplitudes are detected if the coefficient of variation $Var(Z_P)$ is determined between the first minimum and maximum premature contraction pulse period threshold values (APC-$1_{min}$, APC-$1_{max}$) or the coefficient of variation $Var(Z_A)$ is determined between the second minimum and maximum premature contraction pulse amplitude threshold values (APC-$2_{min}$, APC-$2_{max}$);

h) determining, through the type determination module, a tachycardia if the pulse period average Mean $(PP_i)$ is less than a minimum pulse period threshold value $(PP_{min,\ TC})$;

i) determining, through the type determination module, a bradycardia if the pulse period average Mean $(PP_i)$ is greater than a maximum pulse period threshold value $(PP_{max,\ BC})$; and j) determining, through the type determination module, and classifying a non-specified arrhythmia if the arrhythmia cannot be determined in the step e, the step g, the step h, and the step i.

2. The arrhythmia detecting method of claim 1, wherein a number of the plurality of pulse periods is n-1, the number of the similarity statistical comparison values corresponding to the similarities of the pulse periods is $$\frac{1}{2} * \binom{n-1}{2},$$

a number of the plurality of pulse amplitudes is n, and the number of the similarity statistical comparison values corresponding to similarities of the pulse amplitudes is $$\frac{1}{2} * \binom{n}{2}.$$

3. The arrhythmia detecting method of claim 2, where the step b is to compare, through the comparison generating module, the similarities of any two pulse periods by a pulse period comparison equation, the pulse period comparison equation is: $(1-K)*PP_i < PP_j < (1+K)*PP_i$, wherein K is 0.02 to 0.2, PP is the pulse period, $PP_i$ is one of the two compared pulse periods and i is a positive integer from 1 to n, $PP_j$ is another one of the two compared pulse periods and j is a positive integer from 1 to n.

4. The arrhythmia detecting method of claim 2, where the step b is to compare, through the comparison generating module, the similarities of any two pulse amplitudes by a pulse amplitude comparison equation, the pulse amplitude comparison equation is $(1-L)*A_i < A_j < (1+L)*A_i$, wherein L is 0.005 to 0.25, A is the pulse amplitude, $A_i$ is one of the two compared pulse amplitudes and i is a positive integer from 1 to n, $A_j$ is another one of the two compared pulse amplitudes and j is a positive integer from 1 to n.

5. The arrhythmia detecting method of claim 3, where the step b is to sequentially input any two of the pulse periods into the pulse period comparison equation through the comparison generating module, to determine the two input pulse periods are similar and generate the similarity statistical comparison value as 1 when the pulse period comparison equation is satisfied, and to determine the two input pulse periods are dissimilar and generate the similarity statistical comparison value as 0 when the pulse period comparison equation is not satisfied.

6. The arrhythmia detecting method of claim 4, where the step b is to sequentially input any two of the pulse amplitudes into the pulse amplitude comparison equation through the comparison generating module, to determine the two input pulse amplitudes are similar and generate the similarity statistical comparison value as 1 when the pulse amplitude comparison equation is satisfied, and to determine the two input pulse amplitudes are dissimilar and generate the similarity statistical comparison value as 0 when the pulse amplitude comparison equation is not satisfied.

7. The arrhythmia detecting method of claim 3, wherein the pulse period sequence or the pulse amplitude sequence are detected by an electronic sphygmomanometer.

8. The arrhythmia detecting method of claim 4, wherein the pulse period sequence or the pulse amplitude sequence are detected by an electronic sphygmomanometer.

9. The arrhythmia detecting method of claim 3, wherein the pulse period sequence and the pulse amplitude sequence are detected by mechanical pressure, optical pulse wave or acoustic pulse detection.

10. The arrhythmia detecting method of claim 4, wherein the pulse period sequence and the pulse amplitude sequence are detected by mechanical pressure, optical pulse wave or acoustic pulse detection.

11. An arrhythmia detection apparatus (1), comprising:
a cuff (12), wrapping an arm of subjects for measuring a pulse sequence;
a processing unit (11), electrically connected to the cuff (12), and comprising:
an analog to digital conversion module (111), executing an analog to digital conversion to the pulse sequence;
a pulse period and pulse amplitude measurement module (112), obtaining a pulse period sequence comprising a plurality of pulse periods and a pulse amplitude sequence comprising a plurality of pulse amplitudes from the digitized pulse sequence;
a comparison generating module (113), sequentially comparing similarities of any two of the pulse periods and any two of the pulse amplitudes and respectively generating similarity statistical comparison values based on compared results of the pulse periods and compared results of the pulse amplitudes, wherein each of the generated similarity statistical comparison values is 1 if the two compared pulse periods or the two compared pulse amplitudes are determined similar, and each of the generated similarity statistical comparison values is 0 if the two compared pulse periods or the two compared pulse amplitudes are determined dissimilar;

a judgment generating module (114), calculating a statistic value comprising a set of the similarity statistical comparison values corresponding to the similarities of the pulse periods and another statistic value comprising a set of the similarity statistical comparison values corresponding to the similarities of the pulse amplitudes, and establishing an arrhythmia analysis matrix based on the calculated statistic values, the pulse period sequence and the pulse amplitude sequence, the arrhythmia analysis matrix (AAM) is $$\begin{bmatrix} ZP \\ ZA \\ PPi \\ Ai \end{bmatrix},$$

where $Z_P$ is the statistic value comprising the set of the similarity statistical comparison values corresponding to the similarities of the pulse periods; $Z_A$ is the statistic value comprising the set of the similarity statistical comparison values corresponding to the similarities of the pulse amplitudes; $PP_i$ is the pulse period sequence, and $A_i$ is the pulse amplitude sequence; and a type determination module (115), determining one of the following conditions in accordance with the AAM and a unique threshold statistical analysis:

determining an atrial fibrillation when a coefficient of variation $Var(Z_P)$ is determined greater than a first atrial fibrillation threshold value AF-1, a pulse period average Mean ($PP_i$) is determined greater than a second atrial fibrillation threshold value $PP_{min, AF}$ or a coefficient of variation $Var(Z_A)$ is determined between minimum and maximum atrial fibrillation threshold values (AF-$2_{min}$, AF-$2_{max}$);

determining if multitude continuous dissimilar pulse periods exist or not when the coefficient of variation $Var(Z_P)$ is determined between first minimum and maximum premature contraction pulse period threshold values (APC-$1_{min}$, APC-$1_{max}$), or the coefficient of variation $Var(Z_A)$ is determined between second minimum and maximum premature contraction pulse amplitude threshold values (APC-$2_{min}$, APC-$2_{max}$), and determining a premature contraction if multitude continuous dissimilar pulse periods are detected;

determining a tachycardia if the pulse period average Mean ($PP_i$) is determined less than a minimum pulse period threshold value ($PP_{min, TC}$);

determining a bradycardia if the pulse period average Mean ($PP_i$) is determined less than a maximum pulse period threshold value ($PP_{max, BC}$);

wherein, the type determination module (115) determines and classifies a non-specified arrhythmia if the arrhythmia cannot be determined in above analysis.

12. The arrhythmia detection apparatus of claim 11, wherein a number of the plurality of pulse periods is n−1, a number of the similarity statistical comparison values corresponding to the similarities of the pulse periods is $$\frac{1}{2}*\binom{n-1}{2},$$

a number of the plurality of pulse amplitudes is n, and a number of the similarity statistical comparison values corresponding to the similarities of the pulse amplitudes is $$\frac{1}{2}*\binom{n}{2}.$$

13. The arrhythmia detection apparatus of claim 12, wherein the comparison generating module (113) compares the similarities of any two of the pulse periods by inputting any two of the pulse periods into a pulse period comparison equation, the pulse period comparison equation is $(1-K)*PP_i < PP_j < (1+K)*PP_i$, wherein K is 0.02 to 0.2, PP is the pulse period, $PP_i$ is one of the two compared pulse periods and i is a positive integer from 1 to n, $PP_j$ is another one of the two compared pulse periods and j is a positive integer from 1 to n.

14. The arrhythmia detection apparatus of claim 12, wherein the comparison generating module (113) compares the similarities of any two of the pulse amplitudes by inputting any two of the pulse amplitudes into a pulse amplitude comparison equation, the pulse amplitude comparison equation is $(1-L)*A_i < A_j < (1+L)* A_i$, wherein L is 0.005 to 0.25, A is the pulse amplitude, $A_i$ is one of the two compared pulse amplitudes and i is a positive integer from 1 to n, $A_j$ is another one of the two compared pulse amplitudes and j is a positive integer from 1 to n.

15. The arrhythmia detection apparatus of claim 13, wherein the comparison generating module (113) sequentially inputs any two of the pulse periods into the pulse period comparison equation, determines the two input pulse periods are similar and generates the similarity statistical comparison value as 1 when the pulse period comparison equation is satisfied, and determines the two input pulse periods are dissimilar and generates the similarity statistical comparison value as 0 when the pulse period comparison equation is not satisfied.

16. The arrhythmia detection apparatus of claim 14, wherein the comparison generating module (113) sequentially inputs any two of the pulse amplitudes into the pulse amplitude comparison equation, determines the two input pulse amplitudes are similar and generates the similarity statistical comparison value as 1 when the pulse amplitude comparison equation is satisfied, and determines the two input pulse amplitudes are dissimilar and generates the similarity statistical comparison value as 0 when the pulse amplitude comparison equation is not satisfied.

17. The arrhythmia detection apparatus of claim 13, wherein the arrhythmia detection apparatus (1) is an electronic sphygmomanometer, and includes:

a power unit (13), electrically connected to the processing unit (11), supplying necessary electric power;

a memory unit (15), electrically connected to the processing unit (11), recording detecting result and detecting data of the arrhythmia detection apparatus (1); and a display unit (14), electrically connected to the processing unit (11), demonstrating the detecting result and detecting data of the arrhythmia detection apparatus (1).

18. The arrhythmia detection apparatus of claim 14, wherein the arrhythmia detection apparatus (1) is an electronic sphygmomanometer, and includes:

- a power unit (13), electrically connected to the processing unit (11), supplying necessary electric power;
- a memory unit (15), electrically connected to the processing unit (11), recording detecting result and detecting data of the arrhythmia detection apparatus (1); and
- a display unit (14), electrically connected to the processing unit (11), demonstrating the detecting result and detecting data of the arrhythmia detection apparatus (1).

* * * * *